(12) United States Patent
Kerr et al.

(10) Patent No.: US 6,332,293 B1
(45) Date of Patent: Dec. 25, 2001

(54) FLOOR MAT HAVING ANTIMICROBIAL CHARACTERISTICS

(75) Inventors: Robert C. Kerr; James N. Rockwell, both of LaGrange, GA (US)

(73) Assignee: Milliken & Company, Spartanburg, SC (US)

(*) Notice: Subject to any disclaimer, the term of this patent is extended or adjusted under 35 U.S.C. 154(b) by 234 days.

(21) Appl. No.: 09/028,943

(22) Filed: Feb. 24, 1998

Related U.S. Application Data

(60) Provisional application No. 60/039,421, filed on Feb. 28, 1997.

(51) Int. Cl.[7] .................................................. E04F 11/16
(52) U.S. Cl. ................................ 52/177; 428/82; 428/95; 428/96; 8/464; 8/495
(58) Field of Search ................................ 52/177; 428/82, 428/85, 95, 96; 8/464, 495

(56) References Cited

U.S. PATENT DOCUMENTS

| | | |
|---|---|---|
| 3,306,808 | 2/1967 | Thompson . |
| 3,901,014 | 8/1975 | Hiroi et al. . |
| 4,084,615 | 4/1978 | Klein et al. . |
| 4,353,706 | 10/1982 | Burns, Jr. et al. . |
| 4,415,331 | 11/1983 | Dusenbury et al. . |
| 4,435,451 * | 3/1984 | Neubert ................................ 428/15 |
| 4,447,201 | 5/1984 | Knudsen . |
| 4,482,593 | 11/1984 | Sagel et al. . |
| 4,679,859 | 7/1987 | Wilson . |
| 4,701,518 | 10/1987 | Osborn et al. . |
| 4,723,960 * | 2/1988 | Shirasawa et al. ...................... 8/495 |
| 4,741,065 | 5/1988 | Parkins . |
| 4,846,845 | 7/1989 | McBride et al. . |
| 4,886,692 | 12/1989 | Kerr et al. . |
| 5,227,214 | 7/1993 | Kerr et al. . |
| 5,240,530 | 8/1993 | Fink . |
| 5,305,565 | 4/1994 | Nagahama et al. . |
| 5,358,537 * | 10/1994 | Kelley et al. ............................ 8/483 |
| 5,680,826 * | 10/1997 | Nagahama et al. .................. 112/410 |
| 5,702,992 | 12/1997 | Martin et al. . |
| 5,725,705 * | 3/1998 | Nagahama et al. .................. 156/148 |

OTHER PUBLICATIONS

Yasuhiro Washino, *Functional Fibers In Japan*, 1993, Chapters 5, 6, and 7.

* cited by examiner

*Primary Examiner*—Yvonne M. Horton
(74) *Attorney, Agent, or Firm*—Terry T. Moyer; William S. Parks

(57) ABSTRACT

A launderable dust control mat having antimicrobial properties is provided. The mat includes a pile fiber upper surface and a rubber backing surface. Metal based antimicrobial agent, are disposed within both the fiber forming the upper surface and the rubber forming the backing surface thereby providing antimicrobial character to the mat as a whole.

3 Claims, No Drawings

FLOOR MAT HAVING ANTIMICROBIAL CHARACTERISTICS

RELATED BACK

This Application claims the benefit of U.S. Provisional Application 60/039,421 filed Feb. 28, 1997 in the name of Robert C. Kerr and James N. Rockwell the contents of which are incorporated herein by reference.

FIELD OF THE INVENTION

The present invention relates generally to flexible launderable floor mats of the type which have a pile surface on one side and a rubber or rubber-like material on the other side which are suitable to undergo multiple spin washing and drying operations and which have antimicrobial character. More particularly, the invention relates to floor mats wherein an antimicrobial agent has been incorporated into at least one of either the pile surface or backing and is preferably present in both.

BACKGROUND

Dust control mats and other floor coverings having a pile side and a polymeric backing are generally used in access ways where people tend to brush or scrape their feet in order to prevent carrying moisture and/or dirt into other areas of the premises. Normally these mats are located in areas of high pedestrian traffic such as doorways.

The art includes a number of configurations and features for various floor mats. Some patents which are believed to be illustrative of known floor coverings include U.S. Pat. No. 3,306,808 to Thompson, et al. issued Feb. 28, 1967; U.S. Pat. No. 4,741,065 to Parkins issued May 3, 1988; U.S. Pat. No. 4,886,692 to Kerr et al. issued Dec. 12, 1989; U.S. Pat. No. 5,227,214 to Kerr et al. issued Jul. 13, 1993; U.S. Pat. No. 5,240,530 to Fink issued Aug. 31, 1993; and U.S. Pat. No. 5,305,565 to Nagahama et al. issued Apr. 26, 1994; the teaching of all of which are incorporated herein by reference.

As will be appreciated by those of skill in the art, floor mats have conventionally consisted of a plurality of tufts in a primary backing adhered to a vulcanized thermoset rubber backing. Such a backing gives dimensional stability to the fabric surface while maintaining the mat's integrity during industrial wash processing which may involve high speed centrifugal action. The production of launderable floor mats has relied on the use of thermoset rubber backings based on nitrile polymer formulas. While these mats perform very adequately for dirt and moisture removal, it is now recognized that further improvement may be forthcoming in the form of components having antimicrobial properties which are able to retain these antimicrobial characteristics through multiple washings. It is believed that by incorporating the antimicrobial agents within the pile forming yarn and/or the backing, extended activity of the antimicrobial properties of these products may be achieved.

OBJECTS AND SUMMARY

In light of the foregoing, it is a general object of the present invention to provide a dust control mat possessing antimicrobial characteristics.

In that regard, it is an object of the present invention to provide a dust control mat including pile forming yarns including antimicrobial constituents disposed therein.

It is a further object of the present invention to provide a dust control mat having a polymeric backing including antimicrobial constituents disposed therein.

It is a feature of the present invention to provide a pile faced floor mat wherein the pile consists essentially of nylon wherein during the melt polymerization of the nylon a metal based antimicrobial compound has been added so as to result in substantial impregnation of the antimicrobial compound within the nylon fiber structure.

It is a further feature of the present invention to provide a polymer-backed floor mat wherein an antimicrobial compound is added to the backing composition during compounding so as to result in substantial incapsulation of the antimicrobial compound within the polymer backing structure.

It is yet a further feature of the present invention to provide a pile-faced floor mat wherein the pile consists essentially of solution dyed nylon which is sculpted through contact with a fiber degrading composition without causing discoloration of the non-sculpted portions.

DESCRIPTION OF THE PREFERRED EMBODIMENTS

The floor mat according to the present invention preferably includes a polymeric backing, which is adhered during vulcanization to a pile fabric including tufts of synthetic yarn extending therefrom. In the preferred practice, the tufts of synthetic yarn and/or the polymeric backing include an antimicrobial constituent incorporated within the structure of the yarn and/or backing as opposed to having a mere surface treatment. As will be appreciated, such encapsulation is important given the multiple washing cycles which such floor mats must undergo during their useful life.

In one potentially preferred practice according to the present invention, the pile surface is made of nylon 6,6 which has undergone conventional melt polymerization but with the addition of a zinc compound and a phosphorus compound as disclosed in U.S. Pat. No. 4,701,518 issued Oct. 20, 1987 to Osborn et al., the contents of which are incorporated herein by reference. This additive is preferably made so as to form a reaction product in situ containing about 900 ppm of zinc or more based on the theoretical weight of nylon resulting from polymerization of the nylon-forming monomer(s). The nylon with antimicrobial constituents is thereafter preferably subjected to a solution dying operation so as to provide substantially uniform coloration throughout the yarn. The term "yarn" as used herein is a generic term which is intended to cover all yarn and cord-like materials suitable for use in the surface of a pile fabric.

According to another aspect of the potentially preferred embodiment of the present invention, the backing also incorporates an antimicrobial constituent disposed therein. The antimicrobial constituent which is used is preferably a metal or metal based composition. One potentially preferred antimicrobial constituent for use in the polymeric backing is VANCIDE 51Z which is a product of R. T. Vanderbilt in Norwalk, Conn., U.S.A. This formulation is understood to be made up of zinc dimethyldithiocarbonate and zinc 2-mercaptobenzothiazole. Although such a zinc-based composition may be preferred, it is likewise contemplated that compositions based on 2 0 other metal systems including silver, copper, metal oxides, metal sulfides, metal chlorides, sodium salts, and metal bearing ceramics (zeolites, silica, glass) may likewise be utilized if desired. The polymeric backing is preferably based on a rubber or rubber-like material such as, by way of example only and not limitation, acrylonitrile-butadiene rubber (NBR) styrene butadiene rubber (SBR), hydrogenated NBR and carboxylated NBR.

In one potentially preferred practice according to the present invention a masterbatch of the polymer components is first prepared by mixing a base rubber of NBR with various stabilizers and processing agents to yield a masterbatch composition as set forth in Table I

TABLE I

| MATERIAL | PARTS BY WEIGHT |
| --- | --- |
| Rubber (NBR) | 100 |
| Plasticizer | 5 |
| Stabilizer | 2 |
| Processing Aid | 1.75 |
| Antioxidant | 1.2 |

The plasticizer which is used is preferably diisononylphthalate. The stabilizer is preferably trinonylphenolphosphate believed to be available from Uniroyal Chemical under the trade designation Polyguard™. The processing aid is purchased from R. T. Vanderbilt in Norwalk Conn. under the trade designation Vanfree™ AP-2. The antioxidant is purchased from Uniroyal Chemical under the trade designation Octamine™.

Following the mixing of the masterbatch, curative agents and the antimicrobial are added in a second stage mixing process for formation of the green rubber compound of the mat backing. An exemplary composition of the green compound formed in this second stage mixing process is set forth in Table II.

TABLE II

| MATERIAL | PARTS BY WEIGHT |
| --- | --- |
| Master batch rubber blend | 100 |
| Sulfur | 1.25 |
| Stearic Acid | 1 |
| Carbon Black N-550 | 40 |
| Vulkacit Thiaram MS (TMTM) | .05 |
| Zinc Oxide | 5 |
| Blowing Agent | 2.5 |
| Vancide 51Z | 3 |

By way of example only and not limitation, preferred blowing agents may include: azodicarbonamide (Celogen™ AZ-Type blowing agents), hydrazides (Celogen™ OT-Type blowing agents) available from Uniroyal Chemical Inc. in Middlebury Conn. and modified azodicarbonamide available from Bayer Chemical in Akron, Ohio under the trade destination Porofor™ ADC-K.

After the mixing processes are complete, the uncured compound is calendared into a sheet form and may thereafter be assembled with the pile fabric for passage through a press molding apparatus for high temperature and pressure vulcanization. The press molding apparatus may be of any suitable type such as illustrated and described in U.S. Pat. No. 4,447,201 to Knudsen (incorporated herein by reference).

While in the press molding apparatus the mat composite is preferably exposed to temperatures of about 300° F–340° F and pressures in the range of about 20 psig–40 psig. At these temperatures and pressures (to which the mat is exposed for about 3–6 minutes), the backing undergoes vulcanization and is integrated to the pile fabric. The formed mat structure is then preferably passed to a post cure oven operated at a temperature of about 300° F–340° F for 3–6 minutes so as to complete vulcanization and to provide additional stability of the resulting product.

In some applications of use, it may be desirable to apply a sculpted pattern to the pile surface so as to enhance the aesthetic character of the mat. It has been found that through use of pile yarns consisting essentially of solution dyed nylon, that such sculpting may be performed by application of fiber degrading compositions without giving rise to a color degradation or "halo" affect immediately adjacent the sculpted section. Potentially preferred processes and chemical formulations for use in sculpting are disclosed in U.S. Pat. No. 4,415,331 to Dusenbury et al., U.S. Pat. No. 4,353,706 to Burns, Jr. et al., and U.S. Pat. No. 4,846,845 to McBride et al., (all incorporated herein by reference). The preferred apparatus of application of the fiber degrading composition may be a jet dyeing apparatus such as disclosed in U.S. Pat. No. 4,084,615 to Norman E. Klein and William H. Stewart, the disclosure of which is incorporated herein by reference.

In light of the above, it will be appreciated that the present invention provides a washable mat product incorporating anti-microbial compositions in one or more of the components thereof. In addition, this mat may be aesthetically enhanced through application of sculpting process. Accordingly, the present invention represents a new and useful advancement over the state of the art.

While specific embodiments and practices have been illustrated and described in accordance with the present invention, it is to be understood that the invention is not to be limited thereto, since modifications will no doubt be made and other embodiments of the principles of this invention will occur to those of skill in the are to which the invention pertains. Therefore, it is intended to cover any such modifications and other embodiments as incorporated the features of the present invention within the true spirit and scope thereof.

What is claimed is:

1. A launderable dust control mat having antimicrobial properties, the mat comprising: a pile fiber upper surface and a polymer backing surface disposed beneath said pile fiber upper surface, wherein said pile fiber upper surface comprises a plurality of tufts formed from solution dyed nylon yarns incorporating a metal based antimicrobial agent disposed throughout all portions of said yarns and said backing surface includes a metal based antimicrobial agent encapsulated therein, such that both said pile fiber upper surface and said polymer backing surface contribute to the antimicrobial properties of said mat.

2. The invention as in claim 1, wherein the metal based antimicrobial agent encapsulated within said backing surface is a zinc based compound.

3. The invention as in claim 1, wherein said polymer backing surface comprises a rubber material selected from the group consisting of NBR, SBR, hydrogenated NBR and carboxylated NBR.

* * * * *